United States Patent [19]

Mayoral

[11] Patent Number: 4,676,779
[45] Date of Patent: Jun. 30, 1987

[54] MEDICAL ASPIRATOR SYSTEM

[76] Inventor: Armando G. Mayoral, Av. Azteca No. 1237, Col. Azteca, Ensenada, B.C., Mexico

[21] Appl. No.: 838,758

[22] Filed: Mar. 12, 1986

[51] Int. Cl.⁴ .............................................. A61M 1/00
[52] U.S. Cl. ........................................ 604/65; 604/35; 604/45; 604/120; 604/73
[58] Field of Search ...................... 604/30–32, 604/45, 35, 73, 65, 118–120

[56] References Cited

U.S. PATENT DOCUMENTS 3,142,299  7/1964  Henderson .......................... 604/34
3,429,313  2/1969  Romanelli ............................ 604/31
3,955,574  5/1976  Rubinstein .......................... 604/120
4,447,226  5/1984  Mayoral .......................... 604/31 X Primary Examiner—Dalton L. Truluck
Attorney, Agent, or Firm—Harlan P. Huebner

[57] ABSTRACT

A medical aspirator system which includes an automatic valve means, suction pump, waste receptacle and a bypass means to move such blood and other material from a wound or operation area without allowing the blood and other material entry into the automatic valve means. The bypass means utilizes camming operations to open and close air suction and air discharge lines by pinching action.

6 Claims, 13 Drawing Figures

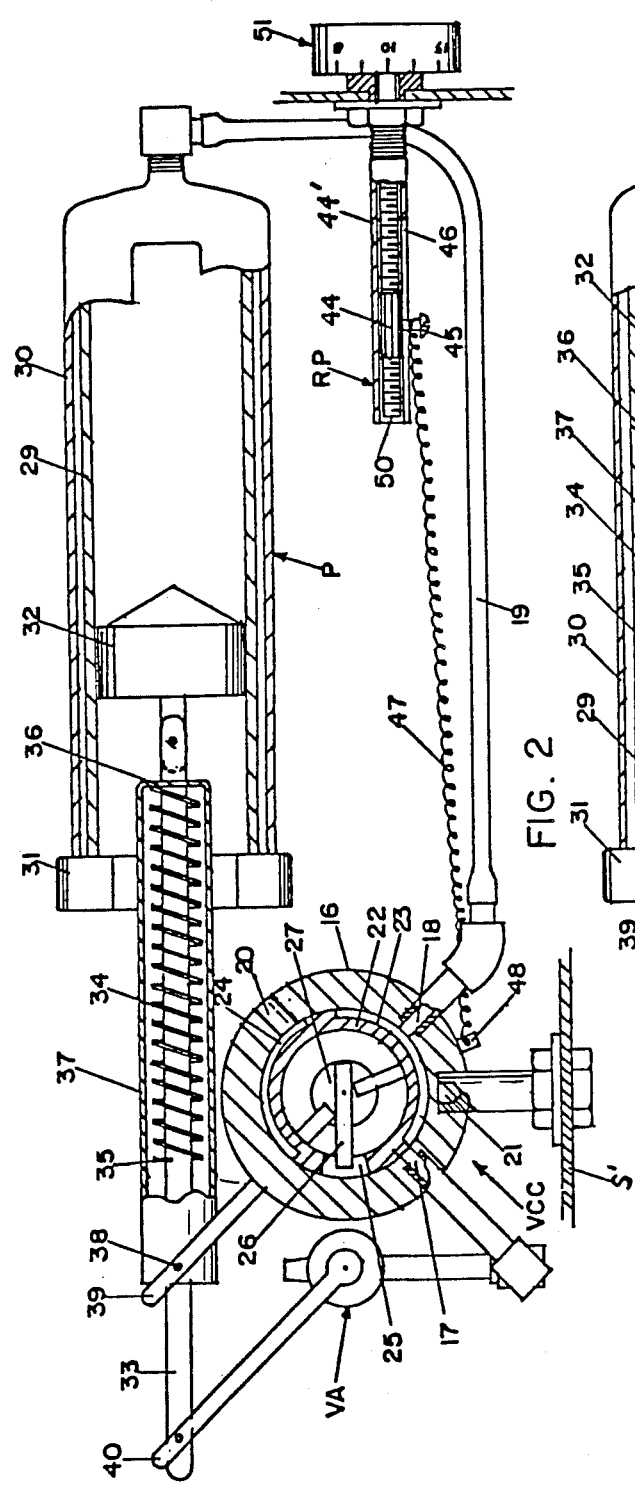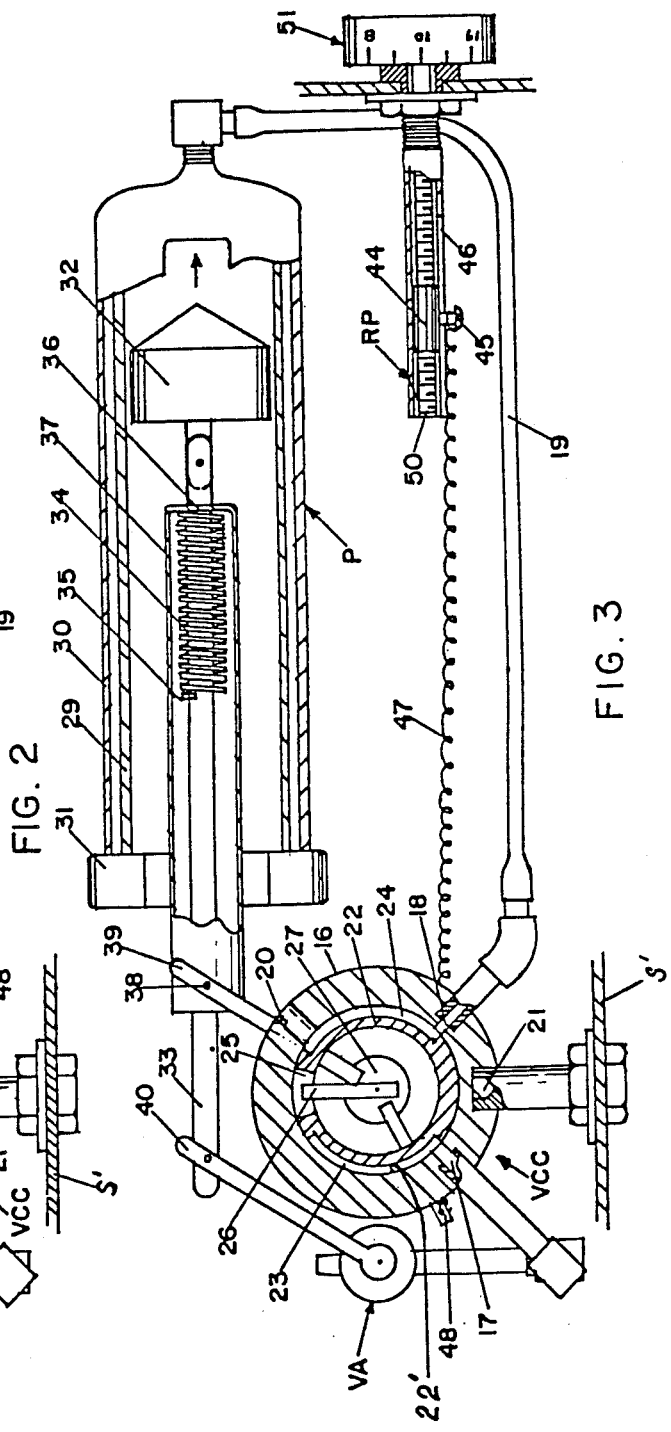

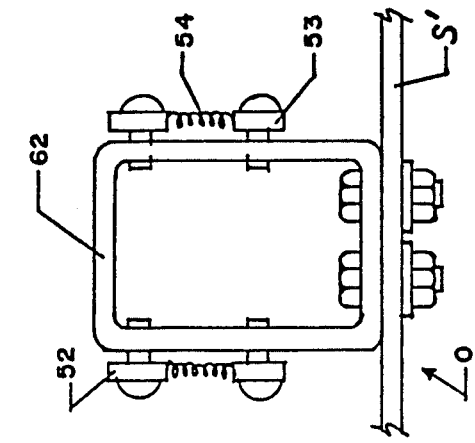
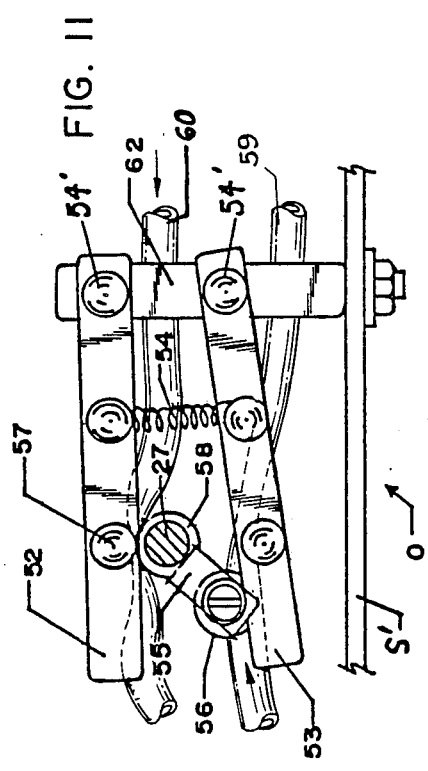
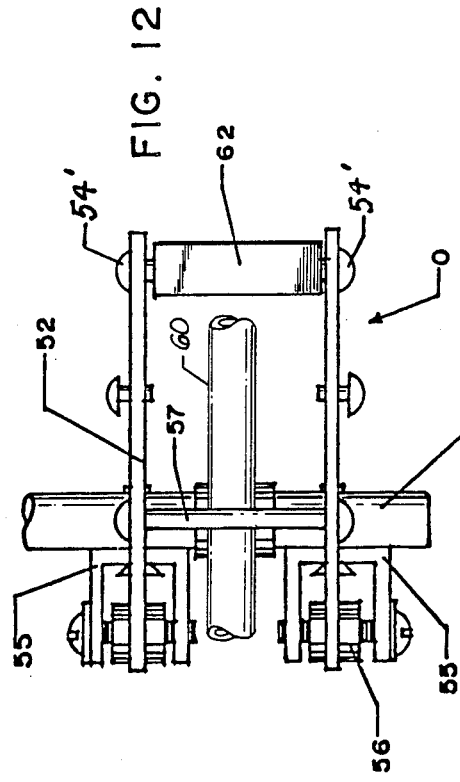
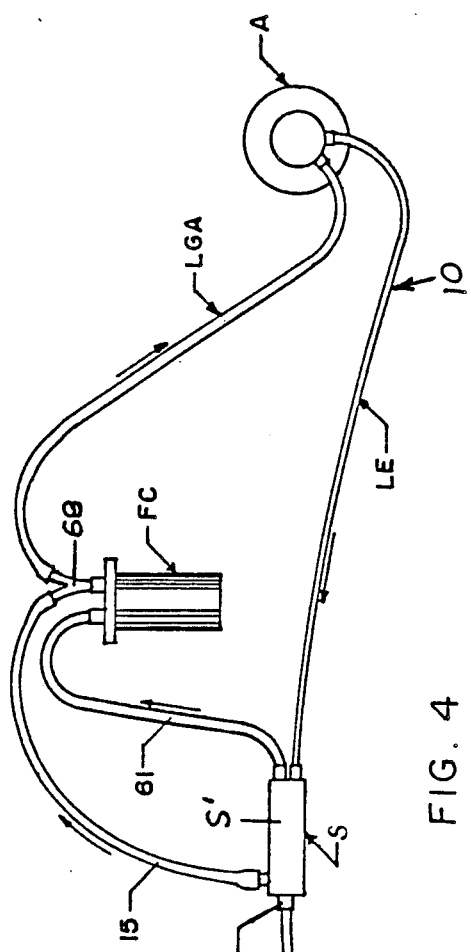
FIG. 13
FIG. 11
FIG. 12
FIG. 4

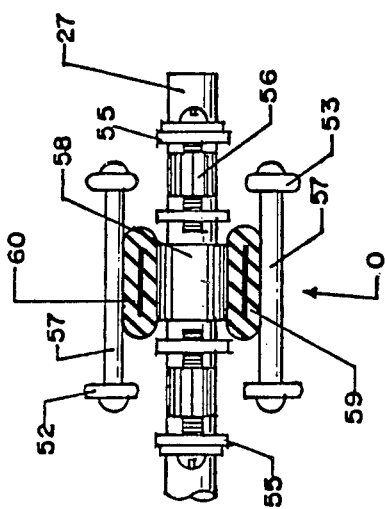
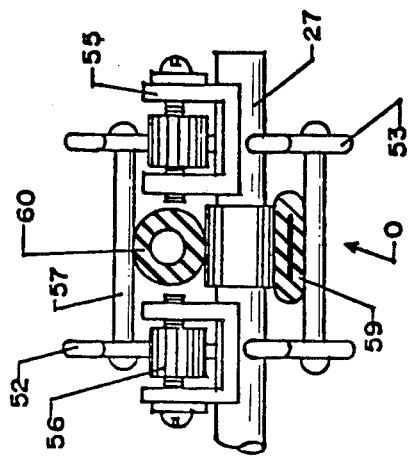
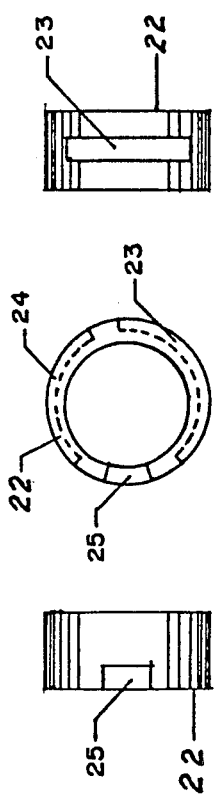
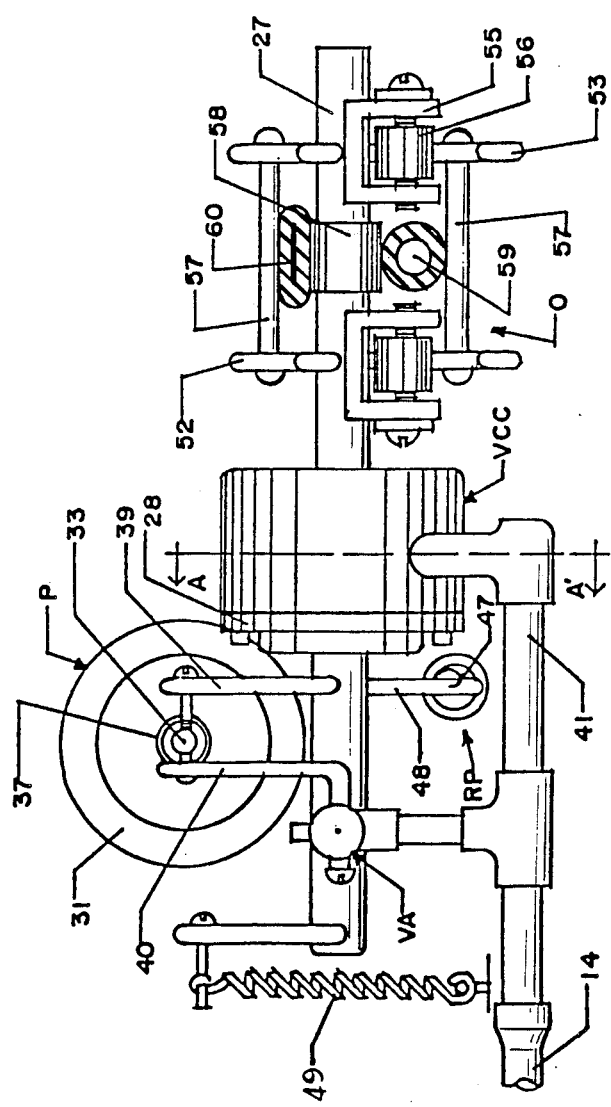

MEDICAL ASPIRATOR SYSTEM

BACKGROUND OF THE INVENTION

1. Field of the invention

This invention relates to a medical aspirator with automatic valve means and bypass means to move blood and other material without passing the same through the automatic valve means.

2. Description of the Prior Art

The present invention is an improvement over the subject matter of U.S. Pat. No. 4,447,226. This patent is directed to a surgical aspirator which operates automatically to remove a blood clot or other material which stops the suction flow of the aspirator.

Aspirators to remove blood and other matter during operations have been known for many years. However, before the advent of the subject matter of U.S. Pat. No. 4,447,226 there was never any successful fully automatic non-cyclical way of removing blood clots or other large pieces of matter that plugged the nozzle of the system. The matter usually had to be removed by hand which could cost valuable time which may be critical during certain operations.

With the advent of U.S. Pat. No. 4,447,226 the removal of obstructions at the nozzle of an aspirator system was automatic. The stoppage caused the system to reverse and instead of suction being applied at the nozzle, air or oxygen was forced out the nozzle and the obstruction was dislodged. The operation is automatic and the reversal of air can be momentary and many time per minute.

While the invention of U.S. Pat. No. 4,447,226 was a breakthrough in automatic aspirators it has a disadvantage that the blood and other matter sucked from the wound or area of the operation has to pass directly through the automatic valve means. Such structure might be susceptible of blockage or malfunction by blood and matter entering the rotating valve means.

Applicant is also aware of U.S. Pat. No. 3,955,574 for a "Pumping System For Catheter Suction Units." This patent was cited as the primary reference against U.S. Pat. No. 4,447,226 but is easily distinguished in that it is a timer type of system whereas U.S. Pat. No. 4,447,226 is non-cyclical and fully automatic when a stoppage occurred.

SUMMARY OF THE INVENTION

It is a purpose of the present invention to provide an automatic valve means in a surgical aspirator system which can close and open depending upon whether there is a blockage of the system and bypass means for moving blood and other matter.

Another object of the invention is to provide a bypass means in the form of tubes or hoses and cam means adjacent automatic valve means wherein blood and other matter may be moved from a wound or operation area for disposal without passing through the valve means.

A still further object is to provide a spring loaded suction responsive trigger means which is insulated from the passage of blood and other matter pumped through said aspirator system.

Another object of the present invention is to include control means to vary the force to rotate the rotatable valve means to correspond with desired suction pressure on air pressure.

A further object of the invention is to provide an aspirator automatic valve mechanism annd valve bypass means which are compact and economical to manufacturer and install in existing systems.

These and other objects and advantages will become apparent from the following part of the specification wherein details have been described for the competence of disclosure, without intending to limit the scope of the invention which is setforth in the appended claims.

BRIEF DESCRIPTION OF THE DRAWINGS

These advantages may be more clearly understood from the following detailed description and by reference to the drawings in which:

FIG. 2 is a cross sectional view of the automatic valve mechanism in an open suction position taken on lines A—A of FIG. 8;

FIG. 3 is a cross sectional view similar to FIG. 2 wherein the valve mechanism is in a closed position where the suction line is closed and a reverse flow of air is being discharged;

FIG. 4 is a view of the surgical aspirator system with nozzle and including a block diagram of the automatic valve mechanism and bypass means;

FIGS. 5, 6 and 7 are various views of the internal rotatable section of said automatic valve mechanism;

FIG. 8 is an end elevational view of the automatic valve mechanism and bypass means affixed thereto with a lower suction tube open and upper air discharge tube closed;

FIG. 9 is an end view of the bypass means of FIG. 8 wherein both lower and upper tubes are closed;

FIG. 10 is an end view of the bypass means of FIG. 8 wherein the lower suction tube is closed and the upper air discharge tube is open;

FIG. 11 is a top plain view of camming means of said bypass means adopted to open and close said suction tube and said air discharge tube;

FIG. 12 is a side elevational view of the camming means of FIG. 11; and

FIG. 13 is an end elevational view of the camming means of FIGS. 11 and 12.

DETAILED DESCRIPTION OF THE PREFERRED EMBODIMENT

Figure 1:
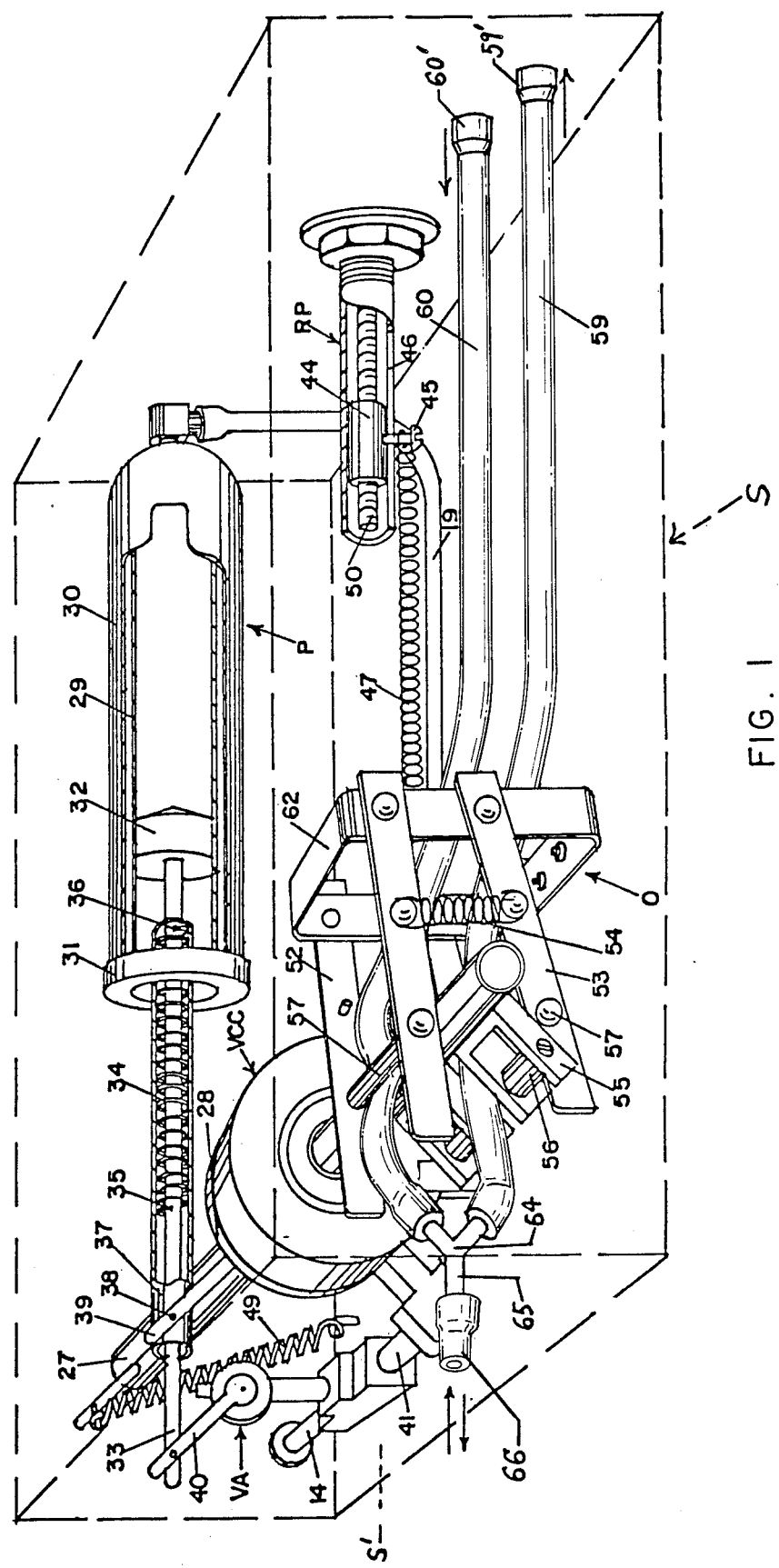
FIG. 1 is a perspective view of an automatic valve mechanism and bypass means of a surgical respirator system.

Turning now to the drawings and particularly FIG. 4 there is illustrated an aspirator system generally designated 10 which is primarily used in surgery. The main innovation of the system 10 is an automatic valve bypass means S, see FIGS. 1 and 4.

Mounted within the means S is a valve means generally designated VCC. A coupling 14 passing out of housing S' is connected to suction line 15. The line 15, see FIG. 4 runs to a blood collection receptacle FC. There is also a line LGA that extends from the receptacle FC to a conventional suction pump A powered by a motor not shown.

The valve means VCC preferably includes an exterior cylindrical stationary portion 16 fabricated from metal or other appropriate material. The portion 16 includes a pair of threaded openings to receive an inlet coupling 17 and outlet coupling 18. The coupling 18 is connected to a spring loaded suction responsive trigger means generally designated P by line 19.

Also extending through the exterior portion 16 is an atmospheric bore 20.

The stationary portion 16 of valve VCC is fixed to a support post 21 which in turn is mounted on the bottom of housing S'.

Within a cylindrical bore 22' of stationary portion 16 is an interior rotatable cylindrical valve section 22 which is preferably fabricated of leaded bronze or other appropriate material. The section 22, see FIGS. 2, 3, 5, 6 and 7, has two annular slots 23 and 24. Each slot 23 and 24 preferably extends annularly around the section 22 less than one half the circumference.

When the apparatus is in a suction mode, see FIG. 2, the rotatable valve section 22 is in a rest position where the couplings 17, 18 and connecting tubes are in communication with each other through groove or slot 23.

Slot 24 when suction is being applied, see FIG. 2, communicates with the atmospheric bore 20.

The rotatable valve section 22 also preferably is formed with a bore 25 to receive an end of a key pin 26 which projects from an elongated shaft 27 which horizontally passes out both sides of the valve VCC, see FIGS. 1 and 8. The shaft 27 is mounted on bearings not seen, in the stationary valve portion 16. Thus, as the interior rotatable valve section 22 rotates the key pin 26 will also rotate and cause the shaft to rotate.

In FIG. 3 the interior rotatable valve section 22 is seen to be rotated 90°, due to blockage of the apparatus to be explained, and the couplings 17 and 18 no longer communicate because the slots 23 and 24 have rotated with 17 communicating with slot 23 and suction is cut off. Also, coupling 18 is now communicating with atmospheric bore 20 through slot 24.

The spring loaded suction responsive trigger means P includes a cylinder 29 preferable made of glass or other appropriate material surrounded by a cylindrical casing 30 of metal or other appropriate material. At one end there is a threaded cover 31 and slidably mounted within cylinder 29 is a piston or plunger 32 which is connected to piston rod 33. The rod 33 is surrounded by a spring 34 and end 35 is attached to the rod.

Surrounding the spring 34 and a portion of rod 33 is a tubular spring housing 37. At the end of housing 37 a lever arm 39 is pivoted at 38 and the arm is in turn secured to shaft 27.

In addition, there is provided a lever arm 40 which is pivotably connected to rod 33 at one end and to a relief valve VA at the other. As the piston 32 and rod 33 move back and forth in the cylinder 29 the relief valve VA will be opened and closed depending on pressure variances at the nozzle 42 and end 43. The valve VA is interposed in line 41 passing from coupling 14 to coupling 17.

Another improvement in the present invention resides in the provision of an air pressure regulator generally designated RP. Secured to the end of housing S' is an outer housing 44' which includes a second tubular adjustment rod 44. Extending from rod 44 is an adjustment pin 45 projecting through slot 46 in rod 44.

Extending from pin 45 is a tension spring 47 which terminates at a tension tab 48 fixed to shaft 27.

The adjustment of the tension on spring 47 will in turn counter balance the tension of trigger means spring 49. The rod 45 through screw means 50 is turned by a graduated scale knob 51.

Upon turning the knob 51, the displacement occurs as described above which places upon spring 47 an increase or decrease in resistance to the negative suction pressure and controls the rotation of shaft 27.

As can be seen the spring 47 will in effect counterbalance the spring 34 whereby the suction moving through line 19 will not allow the piston 32 to move forward in the cylinder 39. The way the piston can move to the FIG. 3 position will be described.

Secured on the shaft 27, see FIGS. 1, 8, 9 and 10 is a fluid bypass means generally designated O. The bypass means O includes a pair of upper pivot arms 52 and a pair of lower pivot arms 53 spaced downward of the arms 52. The arms are pivotably mounted on a rectangular frame 62 which is secured to the bottom of housing S'. Pivot pins 54' retain the respective arms to the frame 62.

As best seen in FIGS. 1, 11 and 13 a pair of tension springs 54 are connected to the upper and lower arms 52 and 53 to bias the same together, yet is flexible enough to allow a spreading of the same upon a camming operation to be next described.

Secured to the shaft 27 are a pair of cam brackets 55 and mounted within the brackets 55 are cam follows 56.

In addition, extending between each upper pair of arms 52 and each lower pair of arms 53 respectively is a pinch bar 57 axially aligned with the shaft 27. The shaft 27 includes a pinch bushing 58 which is aligned beneath the above each bar 57 respectively.

Extending from couplings 59' and 60' mounted on an end of housing S' is suction line 59 and air discharge line 60. The lines 59 and 60 extending through the frame 62 and line 59 passes between the lower pinch bar 57 and pinch bushing 58 while air discharge line 60 passes between the upper pinch bar 57 and pinch brushing 58, see FIGS. 8 through 13.

At the housing S' suction line 61 connects with suction line coupling 59' and air discharge line LE moving from pump A connects to coupling 60'.

Outwardly of the bypass means O the respective lines 59 and 60 are coupled to a Y joint 64 and a single line 65 joins a coupling 66 to a single suction-discharge line 67 passing to nozzle 42.

In operation, the suction pump A is activated and the amount of suction can be varied depending on the type of operation being undertaken. With activation, the end 43 of nozzle 42 is inserted in the opening or wound and suction will pull blood through the nozzle 42, line 67, line 59 and line 61 to the receptacle FC.

With suction passing into receptacle FC, suction is also created at the bifurcation 68 in line 15 through 14, 41 to the valve VCC. With the continued suction in line 14 the valve VCC will remain in the position as seen in FIG. 2. The shaft 27 is positioned for communication between couplings 17 and 18 and the cam brackets being mounted on the shaft 27 will rotate and remain as seen in FIG. 8. That is the suction line 59 will remain open and the pinch bushing 58 will pinch closed air discharge line 60 against upper pinch bar 57 because the arms 53 are forced downward with space between the lower pinch bar 57 and pinch bushing 58.

When the line 60 is closed, air within the line may be purged to the atmosphere through a conventional bypass means (not shown) in suction pump A.

As long as there are no obstructions such as large clots of bloods, tissue, etc. the device will remain and function as described above with no blood passing directly through the valve VCC but only through line 59 of the bypass means O.

Should an obstruction occur at the end 43 of nozzle 42 there will be instantaneously movement and reversal of suction to discharge air or oxygen through ejection air discharge line 60, coupling 66, line 67 to the nozzle end 43 to dislodge the foreign matter.

When suction is interrupted and a negative pressure is presented through lines 15 and 61, the relief valve VA is closed and the pivot arm 40 rotates in turn moving piston 32 to the position shown in FIG. 3 and the suction between couplings 17 and 18 is broken by the rotation of interior section 22 of valve VCC. In turn the shaft 27 will rotate 90° and at 45 both lines 59 and 60, see FIG. 9, are instantaneously closed. Then as the shaft 27 continues rotation the cam followers 56 ride on the arms 53 causing the suction line 59 to close and open the ejection air discharge line 60 so that air or oxygen may conventionally move from pump A to the end 43 of nozzle 42 to eject the blockage.

As the above takes place it can be seen that the valve VCC is completely free of binding or clogging and malfunction because the blood will move through the bypass means O and not the valve VCC or trigger means P.

If upon one reversal of pressure the stoppage or blockage in the nozzle 42 is not cleared, the above described operation is repeated instantaneously so that the stoppage is subject to alternating suction and ejection pressure until it is dislodged or pulled through the nozzle to the receptacle FC.

The invention and its attendant advantages will be understood from the foregoing description and it will be apparent that various changes may be made in the form, construction and arrangements of the parts without departing from the spirit and scope thereof or sacrificing its material advantages, the arrangements hereinbefore described being merely by way of example. I do not wish to be restricted to the specific forms shown or uses mentioned, except as defined in the accompanying claims, wherein various portions have been separated for clarity of reading and not for emphasis.

I claim:

1. In a non-cyclical medical aspirator system adopted to automatically asperate blood and other matter yet able to remove large particles of matter and prevent clogging of said system including a nozzle connected to a combination air suction and air discharge line which includes a portion that moves to a vacuum waste receptacle and continues to a suction pump having motive means to activate said pump, and an air discharge line leading from said pump to discharge air from said pump joining said combination air suction and air discharge line, wherein a housing is interposed within said suction and air discharge line between said nozzle and said waste receptacle, an automatic non-cyclical valve means mounted in said housing including a valve having an air suction and discharge passage and an interior rotatable portion, a pressure responsive trigger means linked to said rotatable portion of said valve, whereby when the suction pressure is reduced caused by a blockage of said system said means will automatically move and rotate said interior rotatable portion and thus reverse the normal suction flow of air to discharge air therefrom through said combination air suction and air discharge line and said nozzle to remove said large particles of matter, the improvement comprising:

a fluid bypass means which is activatable through said automatic non-cyclical valve means which will control the flow of blood and waste material from said nozzle therethrough without passing the same through said valve means and also controls the reversal of air directing air discharge to said nozzle to dislodge said large particles of matter therefrom; and said pressure responsive trigger means is coupled with said automatic non-cyclical valve means separate and apart from said fluid bypass means, whereby when suction pressure is reduced caused by blockage of said system said pressure responsive trigger means will automatically move and rotate said automatic non-cyclical valve means and reverse said normal suction flow to discharge air through said nozzle to remove said particles of matter clogging said system.

2. In a non-cyclical medical aspirator system as defined in claim 1 said automatic non-cyclical valve means includes:

a shaft coupled to said interior rotatable portion for rotation, therewith said fluid shaft projecting from said valve means and engaging said bypass means and said pressure responsive trigger means, whereby activation of said pressure responsive trigger means will rotate said shaft and cause said bypass means to operate.

3. In a non-cyclical medical aspirator system as defined in claim 2 wherein said bypass means includes:

a separate waste suction line and an air discharge line joined to said combination air suction and air discharge line;

camming means activatable by said shaft and engaging said suction line and said air discharge line with a normal operating mode wherein said suction line is open and said air discharge line is cammed closed, a closed mode wherein both of said lines are cammed shut and a stoppage mode wherein said air discharge line is open and said suction line is closed.

4. In a non-cyclical medical aspirator system is defined in claim 3 wherein said camming means includes:

upper and lower cam frame arms one above the other and pivoted for vertical movement;

a cam follower mounted on said shaft engaging at least one of said cam frame arms to bias one cam frame arm from the other;

a pinch bar on each of said cam frame arms one spaced above said shaft and one below said shaft creating a space therebetween for said suction line and said air discharge line respectively, whereby the spaces can be reduced to pinch off one or both of said lines depending upon the rotation of said shaft to assure complete mode change.

5. In a non-cyclical medical aspirator system, as defined in claim 1 wherein that is included:

a pressure regular between said pressure responsive trigger means and said housing, said pressure regular may be set to vary the pressure required to rotate said interior rotatable portion of said valve and to maintain said pressure responsive trigger means in a yieldable suction position.

6. In a non-cyclical medical aspirator system as defined in claim 3 wherein there is included:

a second suction line extending from said non-cyclical valve means to said waste receptacle independent of said waste suction line which line controls activation of said valve and in turn said pressure responsive trigger means.

* * * * *